United States Patent [19]

Sprague et al.

[11] 4,107,175
[45] Aug. 15, 1978

[54] 1,3-BENZODITHIOLANES

[75] Inventors: Peter W. Sprague, Titusville; James E. Heikes, East Windsor, both of N.J.

[73] Assignee: E. R. Squibb & Sons, Inc., Princeton, N.J.

[21] Appl. No.: 751,552

[22] Filed: Dec. 17, 1976

Related U.S. Application Data

[62] Division of Ser. No. 705,849, Jul. 16, 1976.

[51] Int. Cl.$^2$ ............................................. C07D 339/06
[52] U.S. Cl. .......................... 260/327 M; 260/293.57; 260/306.7 R; 260/307 FA; 260/326.5 FL; 260/326.5 SA; 424/246; 424/248.51; 424/250; 424/267; 424/270; 424/272; 424/273 R; 424/274; 544/62; 544/145; 544/377
[58] Field of Search ...................................... 260/327 M

[56] References Cited

U.S. PATENT DOCUMENTS

| | | | |
|---|---|---|---|
| 3,562,290 | 2/1971 | Fawzi | 260/309.2 |
| 3,679,677 | 7/1972 | Takamizawa et al. | 260/247.1 |
| 3,755,363 | 8/1973 | Timmons et al. | 260/327 M |
| 3,884,931 | 5/1975 | Buttner et al. | 260/307 D |

*Primary Examiner*—Cecilia M. Jaisle
*Attorney, Agent, or Firm*—Lawrence S. Levinson; Merle J. Smith; Donald J. Barrack

[57] ABSTRACT

Compounds having the formula

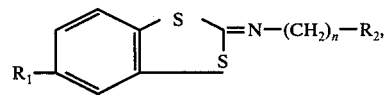

and the pharmaceutically acceptable salts thereof, wherein $R_1$ is hydrogen, halogen, trifluoromethyl, alkyl, alkoxy, nitro, amino, or hydroxy; $R_2$ is carboxyl or alkoxycarbonyl; and $n$ is 0, 1, 2, 3, 4 or 5; have antiinflammatory activity.

21 Claims, No Drawings

1,3-BENZODITHIOLANES

This is a division, of application Ser. No. 705,849, filed July 16, 1976.

SUMMARY OF THE INVENTION 1,3-Benzodirthiolanes having the formula

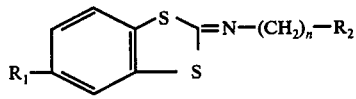

and the pharmaceutically acceptable salts thereof, have antiinflammatory activity. In formula I, and throughout the specification, the symbols are as defined below.

$R_1$ can be hydrogen, halogen, trifluoromethyl, alkyl, alkoxy, nitro, amino or hydroxy;

$R_2$ can be:

i. a group having the formula

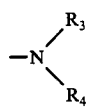

wherein $R_3$ and $R_4$ are the same or different and are hydrogen, alkyl or hydroxyalkyl;

ii. a group having the formula

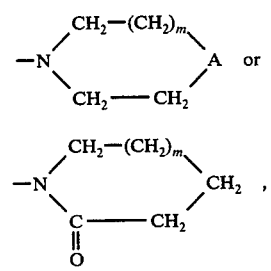

wherein $m$ is 0 or 1, A is oxygen, sulfur, CH—$R_5$ or N—$R_6$, $R_5$ is hydrogen or alkyl and $R_6$ is hydrogen, alkyl, monohydroxyalkyl or phenyl, provided that when $m$ is 0, A is CH—$R_5$;

iii. a group having the formula

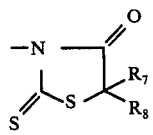

wherein $R_7$ and $R_8$ are each hydrogen or together $R_7$ and $R_8$ are =CH—(CH$_2$)$_p$—$R_9$ wherein p is 0 or an integer from 1 to 9 and $R_9$ is hydrogen, carboxy, alkoxycarbonyl, alkyl, phenyl or phenyl mono- or disubstituted with trifluoromethyl, halogen (preferably fluorine), or alkoxy;

iv. a group having the formula

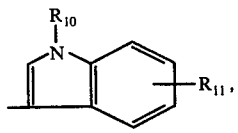

wherein $R_{10}$ is hydrogen, phenylalkyl, halophenylalkyl, benzoyl or halobenzoyl, and $R_{11}$ is hydrogen, halogen or alkoxy; or v. a group having the formula

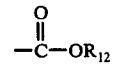

wherein $R_{12}$ can be hydrogen or alkyl; and $n$ is 0, 1, 2, 3, 4 or 5.

The terms "alkyl" and "alkoxy," as used throughout the specification, whether alone, or as part of a larger group, refer to groups having 1 to 4 carbon atoms.

The term "halogen" (or "halo"), as used throughout the specification, whether alone, or as part of a larger group, refers to fluorine, chlorine, bromine and iodine.

Exemplary of the heterocyclic moieties contemplated by the formula

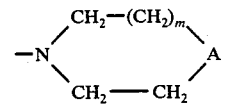

are 1-pyrrolidinyl, 1-piperidinyl, 4-morpholinyl, 4-thiamorpholinyl, 1-piperazinyl, 4-alkyl-1-piperazinyl, 4-alkyl-1-piperidinyl, 3-alkyl-1-pyrrolidinyl, 4-hydroxyalkyl-1-piperazinyl and 4-phenyl-1-piperazinyl.

DETAILED DESCRIPTION OF THE INVENTION

The compounds of this invention can be prepared using as starting materials 1,2,3-benzothiadiazoles having the formula

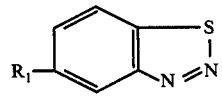

and arylisothiocyanates having the formula

III aryl—N=C=S.

The 1,2,3-benzothiadiazoles of formula II are readily obtainable using, for example, the procedure described by Jacobsen, Ann., 277: 209–261 (1893). Arylisothiocyanates of formula III are well known compounds and are readily obtainable using art recognized procedures; see, for example, Hodgekins, J. Org. Chem., 29: 3098 (1964).

Reaction od a 1,2,3-benzothiadiazole of formula II with an arylisothiocyanate of formula III yields an intermediate having the formula

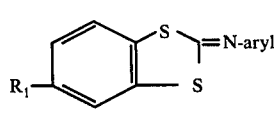

The reaction is run at an elevated temperature (preferably above about 200° C), and preferably in an inert atmosphere such as argon or nitrogen; see Huisgen, Experentia, 17, 566 (1961).

The precursor of a compound of formula I is a quaternary salt of a 1,3-benzodithiolane of formula IV. Quaternization of a compound of formula IV can be accomplished by reacting the compound with an alkylating agent. The particular alkylating agent used is not critical. However, the most readily available (and, therefore, preferred) alkylating agents are those having the formula

wherein $R_{13}$ is a substituted or unsubstituted phenyl group, or an alkyl group, and X is a sulfonyl group or halogen group. Exemplary alkylating agents are methanesulfonate, benzenesulfonate, p-toluenesulfonate, methyl iodide, methyl bromide, methyl fluoride and methyl chloride.

Reaction of a quaternary derivative of a compound of formula IV with a primary amine having the formula

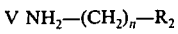

yields a product of formula I. The reaction is preferably run in a polar organic solvent, e.g., dimethylformamide or dimethylsulfoxide, in the presence of a base, e.g., an alkali metal carbonate such as sodium carbonate.

The acid addition salts of the compounds of formula I can be prepared using procedures well known in the art. Exemplary organic and inorganic acids are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, benzenesulfonate and the like.

Many alternative procedures for the preparation of the compounds of this invention will be apparent to the practitioner of this invention. For example, the compounds of formula I wherein $R_2$ is carboxyl can be prepared by saponification of a corresponding compound wherein $R_2$ is alkoxycarbonyl. An alternative method for preparing the compounds of formula I wherein $R_2$ is an N-substituted indole comprises first forming the corresponding indole compound wherein the nitrogen atom is unsubstituted and then using conventional procedures to add the substituent.

The compound of formula I having the formula

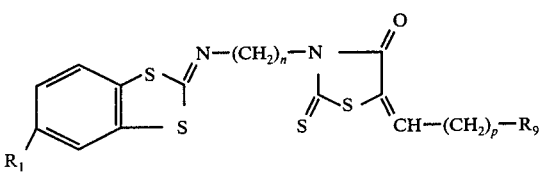

are preferably prepared by reacting an aldehyde having the formula

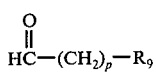

with a corresponding 1,3-benzodithiolane having the formula

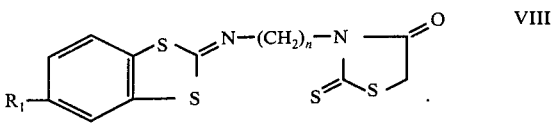

The compounds of formula I and the pharmaceutically acceptable salts thereof can be used in the treatment of inflammation in mammalian species such as rats, dogs, cats, monkeys, etc. Joint tenderness and stiffness (in conditions such as rheumatoid arthritis) can be treated with the abovedescribed compounds. The compounds of this invention can be formulated for use as antiinflammatory agents according to acceptable pharmaceutical practice in oral dosage forms such as tablets, capsules, elixirs or powders or in an injectable form in a sterile vehicle prepared according to conventional pharmaceutical practice. The compounds of this invention can be administered in amounts of 100 milligrams per 70 kilograms of animal body weight per day to 2 grams per 70 kilograms of animal body weight per day, preferably 100 milligrams per 70 kilograms of animal body weight per day to 1 gram per 70 kilograms of animal body weight per day.

The following preparations are included to further describe the preparation of compounds which are useful intermediates in this invention.

PREPARATION 1

5-Chloro-N-methyl-N-phenyl-1,3-benzodithiol-2-iminium iodide

A. 5-Chloro-N-phenyl-1,3-benzodithiol-2-imine

Phenylisothiocyanate (8.8g) and 5-chloro-1,2,3-benzothiadiazole (3.75g) are combined under an inert atmosphere and heated at 220° C until nitrogen evolution ceases. Initial purification of the product is accomplished by dry column chromatography (600g alumina column, benzene solvent). The product is further purified with a methylene chloride wash and recrystallization (twice) from pentane to yield 1.5g of the title compound, melting point 71°–73° C.

B. 5-Chloro-N-methyl-N-phenyl-1,3-benzodithiol-2-iminium iodide

A solution of 5-chloro-N-phenyl-1,3-benzodithiol-2-imine (6.0g) and methyl iodide (50 ml, excess) in 200 ml of dry benzene is heated at 50° C for 72 hours. The reaction mixture is filtered and the resultant solid is washed several times with pentane. The solid product is recrystallized from n-amyl alcohol to yield 4.0g of the title compound, melting point 205°–207° C.

Anal. Calc'd. for $C_{14}H_{11}ClNS_2 \cdot I$: C, 40.06; H, 2.64; N, 3.34; Cl, 8.45; I, 30.24; S, 15.28. Found: C, 40.26; H, 2.84; N, 3.31; Cl, 8.31; I, 29.98; S, 15.07.

PREPARATION 2

5-Chloro-1,3-benzodithiol-2-ylidene-4-fluoro-N-methylbenzaminium iodide

A. N-(5-Chloro-1,3-benzodithiol-2-ylidene)-4-fluorobenzenamine p-Fluorophenylisothiocyanate (25g) and 5-chloro-1,2,3-benzothiadiazole (8.5g) are combined under an inert atmosphere and heated at 220° C until the evolution of nitrogen ceases. Excess p-fluorophenylisothiocyanate is removed in vacuo. The residue is initially purified by column chromatography (600 ml activity III alumina, cyclohexane solvent). The second fraction obtained is divided into two equal portions and purified by dry column chromatography (alumina, benzene/cyclohexane solvent) yielding 3.5g of material. This material is recrystallized three times from pentane to yield 2.8g of the title compound, melting point 101°–102° C.

B. 5-Chloro-1,3-benzodithiol-2-ylidene-4-fluoro-N-methyl-benzaminium iodide

A solution of N-(5-chloro-1,3-benzodithiol-2-ylidene-4-fluorobenzenamine (1.4g) and methyl iodide (10 ml) in benzene (20 ml) is heated at reflux for three weeks. The resultant precipitate is collected by filtration and recrystallized from acetonitrile/benzene to yield 1.9g of the title compound, melting point 205°–206° C.

Anal. Calc'd. for $C_{14}H_{10}ClFINS_2$: C, 38.42; H, 2.30; N, 3.19; S, 14.65; Cl, 8.10; I, 29.01. Found: C, 38.41; H, 2.26; N, 3.15; S, 14.94; Cl, 7.93; I, 29.18.

PREPARATION 3

N-(1,3-Benzodithiol-2-ylidene)-N-methylbenzaminium iodide

A. 2-(Phenylimino)-1,3-benzodithiole

Phenylisothiocyanate (12.15g) and 1,2,3-benzothiodiazole (4.08g) are combined and heated at 200°–220° C under an inert atmosphere until nitrogen evolution ceases. The reaction mixture is initially purified by column chromatography (500 ml activity I alumina, cyclohexane solvent) to yield 2.8g of crude 2-(phenylimino)-1,3-benzodithiole. The crude solid is further purified by column chromatography (30 ml activity I alumina, pentane solvent) to yield 1.9g of the title compound, melting point 67°–68° C.

B.    N-(1,3-Benzodithiol-2-ylidene)-N-methylbenzaminium iodide

A solution containing 2-(phenylimino)-1,3-benzodithiole (2.3g) in 50 ml of methyl iodide is heated at reflux for twenty-four hours. The precipitate obtained is filtered and washed several tims with benzene. The yellow solid is recrystallized from acetonitrile to yield 2.0g of the title compound, melting point 220°–230° C (dec.).

Anal. Calc'd. for $C_{14}H_{12}NS_2$.I: C, 43.64; H, 3.14; N, 3.64; S, 16.65; I, 32.94. Found: C, 43.69; H, 3.25; N, 3.57; S, 16.65; I, 32.68.

PREPARATION 4

N-(5-Methoxy-1,3-benzodithiol-2-ylidene)-N-methylbenzaminium iodide

A. N-(5-Methoxy-1,3-benzodithiol-2-ylidene)benzenamine

A solution of 5-methoxy-1,2,3-benzothiadiazole (5 g) in 50 ml of phenyl isothiocyanate is heated at 220° C under an inert atmosphere until the evolution of nitrogen ceases (about two hours). The excess phenyl isothiocyanate is removed in vacuo. The resultant residue is chromatographed on silica gel (500 ml) eluting with pentane/dichloromethane (4:1). Fractions containing the desired product ($R_f$=0.2, silica gel, benzene) are combined and concentrated in vacuo. The resultant solid is recrystallized from pentane to yield 2.8 g of the title compound, melting point 58°–60° C.

Anal. Calc'd. for $C_{14}H_{11}NOS_2$: C, 61.51; H, 4.06; N, 5.12; S, 23.46. Found: C, 61.46; H, 3.97; N, 5.21; S, 23.68.

B.    N-(5-Methoxy-1,3-benzodithiol-2-ylidene)-N-methylbenzaminium iodide

A solution of N-(5-methoxy-1,3-benzodithiol-2-ylidene)-benzenamine (4.5 g) in 100 ml of methyl iodide is heated at reflux for three days. The resultant precipitate is collected by filtration and recrystallized from acetonitrile/benzene to yield 6 g of the title compound, melting point 199° C.

Anal. Calc'd. for $C_{15}H_{14}NOS_2$. I: C, 43.37; H, 3.40; N, 3.37; S, 15.44; I, 30.57. Found: C, 45.53; H, 3.39; N, 3.48; S, 15.18; I, 30.68.

PREPARATION 5

N-Methyl-N-(5-nitro-1,3-benzodithiol-2-ylidene)benzaminium iodide

A. N-(5-Nitro-1,3-benzodithiol-2-ylidene)benzenamine

A solution of 5-nitro-1,2,3-benzothiadiazole (4.6 g) in 50 ml of phenylisothiocyanate is heated at 220° C under an inert atmosphere until the evolution of nitrogen ceases (approximately three hours). The excess phenylisothiocyanate is removed in vacuo and the resultant residue chromatographed on 1000 ml of silica gel eluting with methylene chloride/pentane (1:4). The fractions containing the desired product are combined and concentrated in vacuo. The resultant solid is recrystallized from cyclohexane to yield 2.1 g of the title compound, melting point 136°–138° C.

Anal. Calc'd. for $C_{13}H_8N_2O_2S_2$: C, 54.15; H, 2.80; N, 9.72; S, 22.24. Found: C, 54.14; H, 2.66; N, 9.84; S, 22.50.

B. N-Methyl-N-(5-nitro-1,3-benzodithiol-2-ylidene)benzaminium iodide

A solution of N-(5-nitro-1,3-benzodithiol-2-ylidene)-benzenamine (5 g) and methyl iodide (20 ml, excess) in benzene (100 ml) is heated at reflux for 2.5 weeks. The resulting slurry is filtered and recharged with methyl iodide every three days. The combined collected precipitate is recrystallized from acetonitrile/benzene to yield 4.0g of the title compound, melting point 210° C.

Anal. Calc'd. for $C_{14}H_{11}N_2O_2S_2$. I: C, 39.08; H, 2.58; N, 6.51; S, 14.90; I, 29.49. Found: C, 39.36; H, 2.60; N, 6.74; S, 15.15; I, 29.68.

PREPARATION 6

N-Methyl-N-[5-(trifluoromethyl)-1,3-benzodithiol-2-ylidene]-benzminium iodide

A. N-[5-(Trifluoromethyl)-1,3-benzodithiol-2-ylidene]-benzenamine

Anal. Calc'd. for $C_{12}H_{16}N_2S_2 \cdot 2HCl \cdot H_2O$: C, 41.98; H, 5.87; N, 8.16; S, 18.68; Cl, 20.65. Found: C, 41.76; H, 6.17; N, 7.96; S, 18.48; Cl, 20.37.

EXAMPLE 19

N'-(1,3-Benzodithiol-2-ylidene)-N,N-dibutyl-1,2-ethanediamine

A solution of N-(1,3-benzodithiol-2-ylidene)-N-methylbenzaminium iodide (11.55g), N,N-dibutyl-1,2-ethanediamine (5.16g) and anhydrous sodium carbonate (1.59g) in 200 ml of anhydrous dimethylformamide is heated at 120° C for two hours and left A solution of 5-(trifluoromethyl)-1,2,3-benzothiadiazole (5 g) in 50 ml of phenylisothiocyanate is heated at reflux under an inert atmosphere until the evolution of nitrogen ceases (approximately 3 hours). The excess phenyl isothiocyanate is removed by distillation. The residue is chromatographed on 1000 ml of silica gel eluting with pentane/dichloromethane (4:1). Fractions containing the desired product are combined and concentrated in vacuo. The resultant solid is recrystallized from hexane to yield 4 g of the title compound, melting point 122°–123° C.

Anal. Calc'd. for $C_{14}H_8F_3NS_2$: C, 54.01; H, 2.59; N, 4.50; S, 20.59; F, 18.31. Found: C, 54.22; H, 2.45; N, 4.52; S, 20.74; F, 18.11.

B. N-Methyl-N-[5-(trifluoromethyl)-1,3-benzodithiol-2-ylidene]-benzenaminium iodide A solution of N-[5-(trifluoromethyl)-1,3-benzodithiol-2-ylidene]benzenamine (2.4 g) and methyl iodide (20 ml, excess) in 100 ml of benzene is heated at reflux for 2.5 weeks. The reaction mixture is filtered and recharged with methyl iodide every three days. The combined precipitates (3.3g) are recrystallized from acetonitrile/benzene. The recrystallized product is dried in vacuo at 100° C for three days to yield 3.0g of the title compound, melting point 161°–164° C.

Anal. Calc'd. for $C_{15}H_{11}NS_2F_3I \cdot 0.5\ C_6H_6$: C, 43.90; H, 2.87; N, 2.84; S, 13.02; I, 25.79. Found: C, 43.84; H, 2.68; N, 2.91; S, 13.22; I, 25.90.

PREPARATIONS 7-10

Following the procedure of preparation 1, but substituting the compound listed in column I for 5-chloro-1,2,3-benzothiadiazole yields the compound listed in column II.

| Column I | Column II |
| --- | --- |
| 7. 5-methyl-1,2,3-benzothiadiazole | 5,N-dimethyl-N-phenyl-1,3-benzodithiol-2-iminium iodide |
| 8. 5-amino-1,2,3 benzothiadiazole | 5-amino-N-methyl-N-phenyl-1,3-benzodithiol-2-iminium iodide |
| 9. 5-hydroxy-1,2,3-benzothiadiazole | 5-hydroxy-N-methyl-N-phenyl-1,3-benzodithiol-2-iminium iodide |
| 10. 5-bromo-1,2,3-benzothiadiazole | 5-bromo-N-methyl-N-phenyl-1,3-benzodithiol-2-iminium iodide |

The following examples are specific embodiments of this invention.

EXAMPLE 1

[(1,3-Benzodithiol-2-ylidene)amino]acetic acid, ethyl ester

A solution of N-(1,3-benzodithiol-2-ylidene)-N-methylbenzaminium iodide (3.85g), 2-amino-acetic acid ethyl ester, hydrochloride (1.40g), and anhydrous potassium carbonate (1.38g) in 200 ml of anhydrous dimethylformamide is heated at 120° C under a nitrogen atmosphere for two hours. The reaction mixture is then poured into two liters of distilled water and extracted with three 300 ml portions of benzene. The combined benzene extracts are dried over anhydrous sodium sulfate and concentrated in vacuo to yield 2.5g of crude product, which is chromatogrphed on 600 ml of silica gel, eluting first with pentane/dichloromethane (1:1) and finally with dichloromethane. The product with $R_f=0.32$ (silica gel, 2% ethyl acetate/dichloromethane) is recrystallized from pentane to yield 1900 mg of the title compound, melting point 88°–89° C.

Anal. Calc'd. for $C_{11}H_{11}NO_2S_2$: C, 52.15; H, 4.38; N, 5.53; S, 25.31. Found: C, 52.38; H, 4.45; N, 5.53; S, 25.13.

EXAMPLE 2

3-[(1,3-Benzodithiol-2-ylidene)amino]propanoic acid, ethyl ester

A solution of N-(1,3-benzodithiol-2-ylidene)-N-methyl benzaninium iodide (11.55g), 3-aminopropanoic acid, ethyl ester hydrochloride (4.61g) and anhydrous sodium carbonate (3.18g) in 400 ml of anhydrous dimethylformamide is heated at 120° C under a nitrogen atmosphere for 2 hours. The reaction mixture is poured into 3 liters of distilled water and extracted with three 500 ml portions of benzene. The combined benzene extracts are dried over anhydrous sodium sulfate and concentrated in vacuo to yield an oil. The oil is chromatographed on 1000 ml of silica gel, eluting first with pentane/dichloromethane (1:1) and finally dichloromethane. The produce obtained with $R_f=0.35$ (silica gel/2% ethyl acetate:dichloromethane) is recrystallized from pentane to yield 2.3g of the title compound, melting point 61°—62° C.

Anal. Calc'd. for $C_{12}H_{13}NO_2S_2$: C, 53.91; H, 4.90; N, 5.24; S, 23.99; Found: C, 53.80; H, 4.89; N, 5.23; S, 23.90.

EXAMPLE 3

[(1,3-Benzodithiol-2ylidene)amino]acetic acid

A solution of [(1,3-benzodithiol-2-ylidene) amino]-acetic acid ethyl ester (2.5g, prepared as described in Example 1) and potassium hydroxide (550 mg) in 500 ml of anhydrous methyl alcohol is stirred at room temperature for 120 hours. The reaction mixture is then concentrated in vacuo. The resultant solid residue is triturated with diethyl either to remove unreacted starting material. The undissolved residue is then dissolved in 50 ml of water and filtered through Celite. The aqueous solution is treated with 10% hydrochloric acid until the pH is 5. The resultant precipitate is collected by filtration and dried in vacuo over phosphorous pentoxide at 60° C for about 16 hours. The dried solid is recrystallized twice from ethyl acetate to yield 1.3g of the title compound, melting point 195°–200° C.

Anal. Calc'd. for $C_9H_7NO_2S_2$: C, 47.98; H, 3.13; N, 6.22; S, 28.47. Found: C, 48.22; H, 3.10; N, 6.26; S, 28.26.

EXAMPLE 4

3-[(1,3-Benzodithiol-2-ylidene)amino]propanoic acid

A solution of 3-[(1,3-benzodithiol-2ylidene)amino]-propanoic acid, ethyl ester (3.0g, prepared as described in Example 2) and sodium hydroxide (499 mg) in 120 ml of absolute ethanol is stirred at room temperature for 120 hours. The reaction mixture is concentrated in vacuo, and the resultant solid residue is washed with diethyl ether to remove unreacted starting material. The crude reaction product is dissolved in 50 ml of water, filtered through Celite, and the aqueous solution is then treated with 10% hydrochloric acid until the pH is 5. The resultant precipitate is collected by filtration and dried in vacuo at 60° C overnight. Recrystallization of the dried product from n-pentyl alcohol yields 1.9g of the title compound, melting point 203–204° C.

Anal. Calc'd. for $C_{10}H_9NO_2S_2$: C, 50.19; H, 3.79; N, 5.85; S, 26.80. Found: C, 50.29; H, 3.99; N, 5.72; S, 26.77.

EXAMPLE 5

4-[(1,3-Benzodithiol-2-ylidene)amino]butanoic acid, ethyl ester

A solution of N-(1,3-benzodithiol-2-ylidene)-N-methylbenzaminium iodide (11.55g), 4-aminobutanoic acid, ethyl ester, hydrochloride (5.04g) and anhydrous sodium carbonate (3.18g) in 300 ml of anhydrous dimethylformamide is heated at 130° C under a nitrogen atmosphere for 3 hours. The reaction mixture was poured into 1000 ml of water and extracted with three 300 ml portions of benzene. The combined benzene extracts are washed with two 500 ml portions of water, dried over sodium sulfate, and concentrated in vacuo.

The resultant yellow oil is chromatographed on silica gell (900 ml) using dichloromethane/petane (1:1) as eluent. The product with $R_f=0.42$ (silica gel/dichloromethane) is recrystallized from petane to yield 1.8g of the title compound, melting point 35°–36° C.

Anal. Calc'd. for $C_{13}H_{15}NO_2S_2$: C, 55.49; H, 5.37; N, 4.98; S, 22.79. Found: C, 55.60; H, 5.55; N, 5.03; S, 22.67.

EXAMPLE 6

[(1,3-Benzodithiol-2-ylidene)amino]butanoic acid

A solution of 4-[(1,3-benzodithiol-2-ylidene)amino]-butanoic acid, ethyl ester (3g, prepared as described in Example 5) and sodium hydroxide (427 mg) in 80% aqueous ethanol (50 ml) is stirred at room temperature for seven days. The reaction mixture is concentrated in vacuo and the residue triturated with two 50 ml portions of hot benzene. The solid residue is dissolved in 100 ml of water, filtered through Celite, and the filtrate treated with 10% hydrochloric acid until the pH is 4. The solid precipitate is collected by filtration and washed on the filter with water. Recrystallization of the solid product from chloroform yields 1.3g of the title compound, melting point 140°–142° C.

Anal. Calc'd. for $C_{11}H_{11}NO_2S_2$: C, 52.15; H, 4.38; N, 5.53; S, 25.31. Found: C, 52.27 H, 4.43; N, 5.73; S, 25.02.

EXAMPLE 7

3-[(1,3-Benzodithiol-2-ylidene)amino]propanoic acid, methyl ester

A solution of N-(1,3-benzodithiol-2-ylidene)-N-methylbenzaminium iodide (11.55g), 3-aminopropanoic acid, methyl ester hydrochloride (4.19g) and anhydrous sodium carbonate (3.18g) in 300 ml of anhydrous dimethylformamide is heated at 120° C under nitrogen for three hours. The reaction mixture is poured into water (1000 ml) and extracted with three 200 ml portions of benzene. The combined benzene extracts are washed with water and brine, dried over anhydrous sodium sulfate, and concentrated in vacuo to yield 13.0g of crude product. This product is chromatographed on silica gel (1000 ml) eluting with 1) pentane (2000 ml); 2) dichloromethane/pentane (4000 ml, 1:1); and 3) dichloromethane (6000 ml). The fractions containing the product with $R_f=0.38$ (silica gel/dichloromethane) are combined and concentrated in vacuo.

The resultant solid is recrystallized from pentane to yield 3.65g of the title compound, melting point 58°–60° C.

Anal. Calc'd. for $C_{11}H_{11}NO_2S_2$: C, 52.15; H, 4.38; N, 5.53; S, 25.31. Found: C, 52.43; H, 4.50; N, 5.45; S, 25.54.

EXAMPLE 8

3-[(1,3-Benzodithiol-2-ylidene)amino]propanoic acid, 1-methylethyl ester

A solution of N-(1,3-benzodithiol-2-ylidene)-N-methylbenzaminium iodide (11.55g), 3-aminopropanoic acid, isopropyl ester, hydrochloride (5.03g) and anhydrous sodium carbonate (3.18g) in 300 ml of anhydrous dimethylformamide is heated at 120° C under nitrogen for 3 hours. The reaction mixture is poured into water (1000 ml) and extracted with three 200 ml portions of benzene. The combined benzene extracts are washed with water and brine, dried over anyhdrous sodium sulfate, and concentrated in vacuo to yield 10.0 g of crude product. The crude product is chromatographed on silica gel (1000 ml) eluting with 1) pentane (1000 ml); 2) pentane/dichloromethane (1.1, 4000 ml); and 3) dichloromethane (1000 ml). the fractions containing the product with $R_f=0.3$ (silica gel/dichloromethane) are concentrated and the resultant solid recrystallized from pentane to yield 2.2g of the title compound, melting point 60°–61° C.

Anal. Calc'd. for $C_{13}H_{15}NO_2S_2$: C, 55.49; H, 5.37; N, 4.98; S, 22.79. Found: C,55.21; H, 5.26; N, 4.91; S, 22.97.

EXAMPLE 9

3-[(1,3-Benzodithiol-2-ylidene)amino]propanoic acid, butyl ester

A solution of N-(1,3-benzodithiol-2-ylidene)-N-methylbenzaminium iodide (11.55g), 3-aminopropanoic acid, n-butyl ester, hydrochloride (5.45g) and anhydrous sodium carbonate (3.18g) in 300 ml of anhydrous dimethylformamide is heated at 120° C under nitrogen for three hours. The reaction mixture is poured into water (1000 ml) and extracted with three 200 ml portions of benzene. The combined benzene extracts are washed with water and brine, dried over anhydrous sodium sulfate, and concentrated in vacuo to yield 12g of crude product. the crude oil is chromatographed on silica gel (1000 ml), eluting with 1) pentane (2000 ml), 2) dichloromethane/pentane (1:1, 4000 ml) and 3) dichloromethane (1000 ml). The fractions containing product with $R_f=0.4$ (silica gel, 1% ethyl acetate, dichloromethane) are combined and concentrated in vacuo. The resultant precipitate is collected by filtration at 4° C to yield 1.3g of the title compound which is an oil at room temperature.

Anal. Calc'd. for $C_{14}H_{17}NO_2S_2$: C, 56.92; H, 5.80; N, 4.74; S, 21.71. Found: C, 56.85; H, 5.93; N, 4.64; S, 21.79.

EXAMPLE 10

3-[(5-Chloro-1,3-benzodithiol-2-ylidene)amino]-butanoic acid, ethyl ester

A solution of 5-chloro-N-methyl-N-phenyl-1,3-benzodithiol-2-iminium iodide (12.59g), 4-aminobutanoic acid, ethyl ester, hydrochloride (5.02g), and anhydrous sodium carbonate (3.18g) in 300 ml of anhydrous dimethylformamide is heated at 120° C under nitrogen for three hours. The reaction mixture is poured into water (1000 ml) and extracted with three 200 ml portions of benzene. The combined benzene extracts are washed with water and brine, dried over sodium sulfate, and concentrated in vacuo. The resultant crude product is chromatographed on silica gel (1000 ml) eluting with 1) pentane (1000 ml), 2) pentane/dichlormethane (1:1, 4000 ml) and 3) dichloromethane (9000 ml). The fractions containing product with $R_f=0.4$ (silica gel, 1% ethyl acetate/dichloromethane) are concentrated in vacuo. The resultant solid is recrystallized from pentance to yield 3.02g of the title compound, melting point 60°–61° C.

Anal. Calc'd. for $C_{13}H_{14}ClNO_2S_2$: C, 49.44; H, 4.47; N, 4.43; Cl, 11.22; S, 20.30. Found: C, 49.71; H, 4.52; N, 4.59; Cl, 11.42; S, 20.54.

EXAMPLE 11

3-[(1,3-Benzodithiol-2-ylidene)amino]butanoic acid, methyl ester

A solution of N-(1,3-benzodithiol-2-ylidene)-N-methylbenzaminium iodide (11.55g), 4-aminobutanoic acid, methyl ester, hydrochloride (4.61g) and anhydrous sodium carbonate (3.18g) in 300 ml of anhydrous dimethylformamide is heated at 120° C under nitrogen for 3 hours. The reaction mixture is poured into water (1400 ml) and extracted with three 200 ml portions of benzene. The combined benzene extracts are washed with water and brine, dried over sodium sulfate, and concentrated in vacuo. The resultant oil is chromatographed on silica gel (1000 ) eluting with 1) pentant (2000 ml), 2) pentane/dichloromethane (1:1, 4000 ml) and 3) dichloromethane (9000 ml). The fractions containing product with $R_f = 0.4$ (silica gel, 1% ethyl acetatedichloromethane) are combined and concentrated in vacuo. The resultant solid is recrystallized from pentane to yield 1.2g of the title compound, melting point 78°-80° C. A second crop gives 1.6g, melting point 78°-80° C.

Anal. Calc'd. for $C_{12}H_{13}NO_2S_2$: C, 53.91; H, 4.90; N, 5.24; S, 23.99. Found: C,53.66; H, 5.18; N, 5.04; S, 23.94.

EXAMPLE 12

3-[(,3-Benzodithiol-2-ylidene)amino]butanoic acid, 1-methylethyl ester

A solution of N-(1,3-benzodithiol-2-N-methylbenzaminium iodide (11.55g), 4-aminobutanoic acid, isopropyl ester, hydrochloride (5.45g) and anhydrous sodium carbonate (3.18g) in 300 ml of anhydrous dimethylformamide is heated at 120° C under nitrogen for 3 hours. The reaction mixture is poured into water (1400 ml) and extracted with three 200 ml portions of benzene. The combined benzene extracts are washed with water and brine, dried over sodium sulfate, and concentrated in vacuo. The resultant oil is chromatographed on silica gel (1000 ml) eluting with 1) pentane (2000 ml), 2) pentane-dichloromethane (4000 ml, 1:1) and 3) dichloromethane (9000 ml). The fractions containing product with $R_f = 0.35$ (silica gel; 1% ethylacetate/dichloromethane) are combined and concentrated in vacuo. The resultant solid is recrystallized from pentane to yield 3.1g of the title compound, melting point 44° C.

Anal. Calc'd. for $C_{14}H_{17}NO_2S_2$: C, 56.92; H, 5.80; N, 4.74; S, 21.71. Found: C, 56.76; H, 5.68; N, 4.65; S, 21.59.

EXAMPLE 13

3-[(1,3-Benzodithiol-2-ylidene)amino]butanoic acid, butyl ester

A solution of N-(1,3-benzodithiol-2-ylidene)-N-methylbanzaminium iodide (11.55g), 4-aminobutanoic acid, n-butyl ester, hydrochloride (5.87g) and anhydrous sodium carbonate (3.18g) in 300 ml of anhydrous dimethylformamide is heated at 120° C under nitrogen for 3 hours. The reaction mixture is poured into water (1400 ml) and extracted with three 200 ml portions of benzene. The combined benzene extracts are washed with water and brine, dried over sodium sulfate, and concentrated in vacuo. The resultant oil is chromatographed on silica gel (1000 ml) eluting with 1) pentane (2000 ml), 2) pentane/dichloromethane (1:1, 4000 ml) and 3) dichloromethane (6000 ml). The fractions containing product with $R_f = 0.45$ (silica gel, 1% ethyl acetate/dichloromethane) are combined and concentrated. The resultant oil is dissolved in pentane and chilled to −20° C. The resultant solid precipitate is collected by filtration at 0° C to yield 3.5g of the title compound, which is an oil at room temperature.

Anal. Calc'd. for $C_{15}H_{19}NO_2S_2$: C, 58.22; H, 6.19; N, 4.53; S, 20.72. Found: C, 58.11; H, 6.01; N, 4.41; S, 20.52.

EXAMPLE 14

3-[(5-Chloro-1,3-benzodithiol-2-ylidene)amino]-propanoic acid, ethyl ester

A solution of 5-chloro-N-methyl-N-phenyl-1,3-benzo-dithiol-2-iminium iodide (9.97g), 3-aminopropanoic acid, ethyl ester, hydrochloride (3.68g) and anhydrous sodium carbonate (2.54g) in 250 ml of anhydrous dimethylformamide is heated at 120° C under nitrogen for 3 hours, then left stirring at room temperature for 2 days. The reaction mixture is poured into water (1400 ml) and extracted with three 200 ml portions of dichloromethane. The combined dichloromethane extracts are washed with three 100 ml portions of water, dried over sodium sulfate, and concentrated in vacuo. The resultant oil is chromatographed on silica gel (1000 ml), eluting with dichloromethane/pentane (1:1). The fractions containing product with $R_f = 0.25$ (silica gel, dichloromethane) are concentrated and the resultant solid recrystallized twice from pentane to yield 1.1g of the title compound, melting point 64°-65° C.

Anal. Calc'd. for $C_{12}H_{12}ClNS_2O_2$: C, 47.75; H, 4.01; N, 4.64; Cl, 11.75; S, 21.25. Found: C, 47.97; H, 4.01; N, 4.74; Cl, 12.01; S, 20.99.

EXAMPLE 15

N'-(1,3-Benzodithiol-2-ylidene)-N,N-dimethyl-1,2-ethanediamine and the dihydrochloride salt thereof A solution of N-(1,3-benzodithiol-2-ylidene)-N-methylbenzaminium iodide (3.85g), dimethylethylenediamine (880 mg), and anhydrous sodium carbonate (530 mg) in 100 ml of dry dimethylformamide is heated at 100° C for two hours, then left stirring at room temperature overnight. The reaction mixture is poured into 800 ml of water and the resultant precipitate is collected by filtration. The white solid contains three major components by thin layer chromatography (silica gel/chloroform). The solid is dissolved in 75 ml of hexane and purified by column chromatography (200 ml of silica gel), eluting with 1) benzene (1000 ml), 2) chloroform (1000 ml) and 3) 10% methanol/chloroform. The solid product obtained by concentration of the fractions eluted with methanol/chloroform are recrystallized from pentane to yield 1.2g of the title compound, melting point 70°-72° C.

Anal. Calc'd. for $C_{11}H_{14}N_2S_2$: C, 55.42; H, 5.92; N, 11.75; S, 26.90. Found: C, 55.67; H, 6.04; N, 11.46; S, 26.83.

EXAMPLE 16

N'-(1,3-Benzodithiol-2-ylidene)-N,N-dimethyl-1,2-ethanediamine, hydrochloride (1:2)

A solution of N'-(1,3-benzodithiol-2-ylidene)-N,N-dimethyl-1,2-ethanediamine (2.0g, prepared as described in Example 15) in 100 ml of diethyl ether is treated dropwise with ethereal hydrogen chloride until precipitation is complete. The white solid thus obtained is filtered, washed with diethyl ether, and recrystallized from acetonitrile. The recrystallized material was filtered and washed with diethyl ether before drying over phosphorous pentoxide for 4 days. Analysis of this product (1.4g) indicates it to be a mixture of mono- and dihydrochloride. The product is recrystallized from ethanol with the addition of 5 ml of etheral hydrogen chloride. The recrystallized solid is filtered under nitrogen, washed with diethyl ether, and dried under nitrogen at atmospheric pressure to yield 1.2g of the title compound, melting point 218°-220° C.

Anal. Calc'd. for $C_{11}H_{14}N_2S_2 \cdot 2HCl \cdot H_2O$: C, 40.12; H, 5.47; N, 8.51; S, 19.47; Cl, 21.53. Found: C, 39.85; H, 5.52; N, 8.43; S, 19.41; Cl, 21.48.

EXAMPLE 17

N'-(1,3-Benzodithiol-2-ylidene)-N,N-dimethyl-1,3-propanediamine

A solution of N-(1,3-benzodithiol-2-ylidene)-N-methyl benzaminium iodide (11.55g), anhydrous sodium carbonate (1.59g) and 3-dimethylaminopropylamine (3.06g) in 200 ml of anhydrous dimethylformamide is heated under a nitrogen atmosphere at 120° C for two hours and left stirring at room temperature for about 16 hours. The reaction mixture is poured into water (2 liters) and extracted three times with 500 ml portions of benzene. The combined benzene extracts are dried over anhydrous sodium sulfate and concentrated in vacuo to yield an oil. This oil is chromatographed on 500 ml of silica gel and eluted with benzene (2 liters), chloroform (2 liters) and finally 10% methanol/chloroform (1 liter). The oil obtained from the 10% methanol/chloroform elution is dissolved in 100 ml of anhydrous diethyl ether and treated with ethereal hydrogen chloride until precipitation is complete. The precipitate is filtered and recrystallized from acetonitrile to yield 8g of dihydrochloride, melting point 201°–205° C. This dihydrochloride is dissolved in 100 ml water and treated with 100 ml of 5% sodium bicarbonate solution. The solution is extracted with 100 ml of dichloromethane. The organic layer is dried over sodium sulfate and concentrated. The solid thus obtained is recrystallized from pentane at −30° C to yield 4g of the title compound, melting point 45.5°–46.5° C. Removal of water from the molecule returns the compound to an oil. Water is needed in the lattice structure for crystallization.

Anal. Calc'd. for $C_{12}H_{16}N_2S_2 \cdot 3/4 H_2O$: C, 54.20; H, 6.63; N, 10.53; S, 24.12. Found: C, 54.22; H, 6.34; N, 10.40; S, 24.16.

EXAMPLE 18

N'-(1,3-Benzodithiol-2-ylidene)-N,N-dimethyl-1,3-propanediamine, hydrochloride (1:2)

A solution of N'-(1,3-benzodithiol-2-ylidene)-N,N-dimethyl-1,3-propenediamine (3.0g, prepared as described in Example 17) in 100 ml of anhydrous diethyl ether is treated dropwise with ethereal hydrogen chloride until precipitation is completed. The resultant solid is collected by filtration under a nitrogen atmosphere, wwashed several times with anhydrous diethyl ether and recrystallized twice from acetonitrile. The recrystallized product is washed with anhydrous diethyl ether and dried at atmospheric pressure under a slow stream of nitrogen to yield 3.1g of the title compound, melting point 188°–190° C.

Anal. Calc'd. for $C_{12}H_{16}N_2S_2 \cdot 2HCl \cdot H_2O$: C, 41.98; H, 5.87; N, 8.16; S, 18.68; Cl, 20.65. Found: C, 41.76; H, 6.17; N, 7.96; S, 18.48; Cl, 20.37.

EXAMPLE 19

N'-(1,3-Benzodithiol-2-ylidene)-N,N-dibutyl-1,2-ethanediamine

A solution of N-(1,3-benzodithiol-2-ylidene)-N-methylbenzaminium iodide (11.55 g), N,N-dibutyl-1,2-ethanediamine (5.16 g) and anhydrous sodium carbonate (1.59 g) in 200 ml of anhydrous dimethylformamide is heated at 120° C for two hours and left stirring at room temperature overnight. The reaction mixture is poured into water (2 liters) and extracted three times with 500 ml portions of benzene. The combined benzene layers are dried over anhydrous sodium sulfate and concentrated. The resultant oil is chromatographed on 500 ml of silica gel eluting with benzene (2 liters), chloroform (2 liters) and finally 10% methanol/chloroform (2 liters). The oil obtained from the elution with 10% methanol/chloroform is dissolved in ether, treated with ethereal hydrogen chloride, and filtered under nitrogen. This hygroscopic solid is dissolved in 5% sodium bicarbonate solution and extracted with dichloromethane. The dichloromethane layer is dried over anhydrous sodium sulfate and concentrated. The resultant oil is dissolved in 15 ml of pentane, treated with charcoal, and filtered. The pentane solution was cooled to −78° C in a dry ice acetone bath. After 24 hours, the white precipitate is quickly filtered and transferred to a flask whereupon the product is returned to an oil. The oil is dried in vacuo at room temperature overnight to yield 2 g of the title compound.

Anal. Calc'd. for $C_{17}H_{26}N_2S_2$: C, 63.31; H, 8.13; N, 8.69; S, 19.88. Found: C, 63.55; H, 8.35; N, 8.59; S, 19.90.

EXAMPLE 20

N'-(1,3-Benzodithiol-2-ylidene)-N,N-dibutyl-1,2-ethanediamine, hydrochloride (1:2)

A solution of N-(1,3-benzodithiol-2-ylidene)-N-methyl-benzaminium iodide (11.55g), N,N-dibutyl-1,3-ethanediamine (5.16g) and anhydrous sodium carbonate (1.59g) in 200 ml of anhydrous dimethylformamide is heated at 120° C under a nitrogen atmosphere for 2 hours, then left stirring at room temperature overnight. The mixture is poured into water (400 ml) and extracted three times with 200 ml portions of benzene. The combined benzene layers are dried over anhydrous sodium sulfate and concentrated in vacuo. The resultant oil is purified by column chromatography (600 ml silica gel) eluting with benzene (200 ml) and finally chloroform (400 ml). The oil obtained from the chloroform elution is dissolved in 200 ml of anhydrous diethyl ether and treated dropwise with ethereal hydrogen chloride until precipitation is complete. The resultant hygroscopic solid is collected by filtration under nitrogen and recrystallized twice from isopropyl alcohol. The product thus obtained is dried at atmospheric pressure over anhydrous phosphorous pentoxide for four days to yield 1.16g of the title compound, melting point 145–147° C.

Anal. Calc'd. for $C_{17}H_{26}N_2S_2 \cdot 2HCl$: C, 49.38; H, 7.31; N, 6.78; S, 15.51; Cl, 17.15. Found: C, 49.61; H, 7.63; N, 6.81; S, 15.64; Cl, 17.06.

EXAMPLE 21

2,2'-[[3-[(1,3-Benzodithiol-2-ylidene)amino]propyl]imino]bisethanol, hydrochloride (1:2)

A solution of N-(1,3-benzodithiol-2-ylidene)-N-methylbenzaninium iodide (11.55g), N-(3-aminopropyl)-diethanolamine (4.8g) and anhydrous sodium carbonate (1.59g) in 200 ml of anhydrous dimethylformamide is heated at 120° C for two hours under a nitrogen atmosphere. The reaction mixture is poured slowly into vigorously stirring ice/water. The mixture is left stirring at 4° C for two hours; however, no precipitation results. The mixture is extracted with three 500 ml portions of benzene. The combined benzene extracts are dried over anhydrous sodium sulfate and concentrated. The resultant oil contains three major products by thin layer chromatography [silica gel, dichloromethane/methanol (9:1) solvent, $R_f$=0.1, 0.5, 0.6]. Initial purification is effected by column chromatography with silica gel (750 ml). Elution with benzene gives the products with $R_f=0.5$ and $R_f=0.6$. Elution with methylene chloride/methanol (7:3) gives the product with $R_f=0.1$. This oil is dissolved in 200 ml of anhydrous diethyl ether and treated dropwise with ethereal hydrogen chloride until precipitation is complete. The hygroscopic solid thus obtained is collected by filtration under nitrogen and recrystallized three times from isopropyl alcohol/methanol (95:5) to yield 1.6g of the title compound, melting point 130–135° C.

Anal. Calc'd. for $C_{14}H_{20}N_2O_2S_2 \cdot 2HCl \cdot H_2O$: C, 41.68; H, 6.00; N, 6.94; Cl, 17.58; S, 15.90. Found: C, 41.87; H, 5.74; N, 6.68; Cl, 17.75; S, 16.06.

EXAMPLE 22

N-(1,3-Benzodithiol-2-ylidene)-1-piperidineethanamine, hydrochloride (1:2)

A solution of N-(1,3-benzodithiol-2-ylidene)-N-methylbenzaminium iodide (11.55g), N-(2aminoethyl)-piperidine (3.84g) and anhydrous sodium carbonate (1:59g) in 200 ml of anhydrous dimethylformamide is heated at 120° C for two hours and left stirring at room temperature overnight. The reaction mixture is poured into 4 liters of water and extracted three times with 300 ml portions of benzene. The combined benzene layers are dried over anhydrous sodium sulfate and concentrated. The resultant oil is chromatographed on 500 ml of silica gel eluting with benzene (2 liters), chloroform (2 liters), and finally 10% methanol/chloroform (2 liters). The solid product obtained from the final elution with 10% methanol/chloroform is recrystallized from pentane. This recrystallization produces a crystalline material which contains two spots by thin layer chromatography (10% methanol/dichloromethane, silica gel). Further purification by recrystallization or column chromatography is unsuccessful. The impure material is dissolved in diethyl ether and treated with ethereal hydrogen chloride until precipitation is complete. The hygroscopic solid is filtered under nitrogen, washed with diethyl ether, and recrystallized from acetontrile. Attempts to dry the sample in vacuo result in the loss of HCl molecules. The procuct is air dried over phosphorous pentoxide to yield 5.3g of the title compound, melting point 186–186.5° C (dec.).

Ana. Calc'd for $C_{14}H_{18}N_2S_2 \cdot 2HCL \cdot 1/2\ H_2O$: C, 46.66; H, 5.87; N, 7.77; Cl, 17.80; S.19.68. Found: C, 46.58H, 5.73; N, 7.77; Cl, 17.87; S, 19.87.

EXAMPLE 23

N-(1,3-Benzodithiol-2-ylidene)-1-piperidineethanamine

A solution of N-(1,3-benzodithiol-2-ylidene)-1-piperidineethanamine, hydrochloride (1:2) (3.2g prepared as described in Example 22) in 50 ml of water is treated with 50 ml of 5% sodium bicarbonate solution and extracted with 100 ml of dichloromethane. After drying over anhydrous sodium sulfate, the dichloromethane solution if concentrated in vacuo to yield a yellow oil which solidifices upon standing. The solid product is recrystallized from pentane to yield 2.4g of product, melting point 70–74° C. It becomres apparent after several attempts to dry the sample in vacuo that the sample is a hydrate. Drying over phosphorous pentoxide produces an oil which immediately solidifies upon exposure to air.

Anal. Calc'd. for $C_{14}H_{18}N_2S_2 \cdot H_2O$: C, 56.72; H, 6.80; N, 9.44; S, 21.63. Found: C, 56.72; H, 6.74; N, 9.15; S, 21.82.

EXAMPLE 24

N-(5-Chloro-1,3-benzodithiol-2-ylidene)-1-piperidineethanamine

A solution of 5-chloro-N-methyl-N-phenyl-1,3-benzodithiol-2-iminium iodide (8.39g), N-(2-aminoethyl)-piperidine (2.56g) and anhydrous sodium carbonate (1.06g) in 200 ml of anhydrous dimethylformamide is heated at 120° C under a nitrogen atmosphere for three hours. The reaction mixture is poured into 1000 ml of water and extracted with three 300 ml portions of dichloromethane. The combined organic extracts are washed with two 500 ml portions of water, dried over anhydrous sodium sulfate, and concentrated in vacuo to yield an oil. This oil is chromatographed on silica gel (1000 ml) eluting with (1) pentane (1000 ml), (2) chloroform (1000 ml), and finally methanol/chloroform (1:4, 2000 ml). The solid product from elution (3) is recrystallized from pentane to yield 4g of the title compound, melting point 42–44° C.

Anal. Calc'd. for $C_{14}H_{17}ClN_2S_2$: C, 53.74; H, 5.48; N, 8.95; Cl, 11.33; S, 20.50. Found: C, 54.03; H, 5.46; N, 9.05; Cl, 11.03; S, 20.32.

EXAMPLE 25

N-(1,3-Benzodithiol-2-ylidene)-4-morpholineethanamine

A solution of N-(1,3-benzodithiol-2-ylidene)-N-methyl-benzaminium iodide (3.85g), N-(aminoethyl)morpholine (1.30g) and anhydrous sodium carbonate (530 mg) in 100 ml of dry dimethylformamide is heated at 100° C for 2 hours, then left stirring at room temperature for about 16 hours. The reaction mixture is poured into 1000 ml of water and extracted three times with benzene. After drying over sodium sulfate, the combine benzene extracts are concentrated to yield an oil which consisted of three major components by thin layer chromatography (silica gel/10% methanol/chloroform. The oil is dissolved in 50 ml of hexane and purified initially by column chromatography (200 ml silica gel) using (1) benzene (1000 ml), (2) chloroform (1000 ml), and (3) 10% methanol/chloroform. The solid product obtained by concentration of the factions eluted with 10% methanol/chloroform is recrystallized from pentane after treating with charcoal to yield 1.7g of the title compound, melting point 75–76° C.

Anal. Calc'd. for $C_{13}H_{16}N_2S_2O_2O$: C, 55.68; H, 5.75; N, 9.99; S, 22.87. Found: C, 55.82; H, 5.90; N, 9.92; S, 22.93.

EXAMPLE 26

N-(1,3-Benzodithiol-2-ylidene)-4-morpholineethanamine, hydrochloride (1:2)

A solution of N-(1,3-benzodithiol-2-ylidene)-N-methylbenzaminium iodide (11.55g), N-(2-aminoethyl)-morpholine (3.90g) and anhydrous sodium carbonate (1.59g) in 100 ml of anhydrous dimethylformamide is heated under a nitrogen atmosphere at 120° C for two hours and left stirring at room temperature for about 16 hours. The reaction mixture is poured into water (4 liters) and extracted three times with 500 ml portions of benzene. The combined organic layers are dried over anhydrous sodium sulfate and concentrated under reduced pressure. The resultant oil is chromatographed on 600 ml of silica gel eluting with benzene (2 liters) and finally chloroform (4 liters). The oil obtained from elution with chloroform is dissolved in 100 ml of diethyl ether and treated with ethereal hydrogen chloride until precipitation is completed. The solid is filtered under nitrogen, washed with diethyl ether, and recrystallized from ethanol. Attempts to dry the sample in vacuo result in loss of HCl molecules. The product is air dried over phosphorous pentoxide to yield 9.1g of the title compound, melting point 211-214° C.

Anal. Calc'd. for $C_{13}H_{16}N_2OS_2 \cdot 2$ HCl $\cdot H_2O$: C, 42.05; H, 5.43, N 7.54; Cl, 19.09; S, 17.27. Found: C, 42.23; H, 5.54; N, 7.61; Cl, 19.36; S, 17.38.

EXAMPLE 27

N-(1,3-Benzodithiol-2-ylidene)-4-morpholinepropanamine

A solution of N-(1,3-benzodithiol-2-ylidene)-N-methylbenzaminium iodide (11.55g), N-(3-aminopropyl)-morpholine (4.32g) and anhydrous sodium carbonate (1.59g) in 200 ml of anhydrous dimethylformamide is heated at 120° C under a nitrogen atmosphere for two hours. The reaction mixture is poured into 1000 ml of ice-water and left at 4° C for two hours. The precipitate is collected by filtration. The solid product is dissolved in dichloromethane, dried over anhydrous sodium sulfate, and concentrated in vacuo to yield 3g of crude product. The solid is recrystallized twice from pentane to yield 1.8g of the title compound, melting point 66-68° C.

Anal. Calc'd. for $C_{14}H_{18}N_2OS_2$: C, 57.11; H, 6.16; N, 9.51; S, 21.78. Found: C, 56.96; H, 5.85; N, 9.58; S, 21.51.

EXAMPLE 28

1-[3-[(1,3-Benzodithiol-2-ylidene)amino]propyl]-2-pyrrolidinone

A solution of N-(1,3-benzodithiol-2-ylidene)-N-methylbenzaminium iodide (3.85g), N-(3-aminopropyl)-2-pyrrolidinone (1.42g) and anydrous sodium carbonate 8530 mg) in 100 ml of anhydrous dimethylformamide is heated at 120° C for two hours. The reaction mixture is poured into one liter of ice-water and after two hours extracted three times with 200 ml portions of benzene. The combined benzene extracts are dried over anhydrous sodium sulfate and concentrated in vacuo. The resultant semi-solid is recrystallized twice from hexane/benzene (90:10) to yield 1.2g of the title compound, melting point 101-104° C.

Anal. Calc'd. for $C_{14}H_{16}N_2OS_2$: C, 57.50; H, 5.52; N, 9.58; S, 21.93. Found: C, 57.62; H, 5.51; N, 9.70; S, 21.67.

EXAMPLE 29

1-[3-[(5-Chloro-1,3-benzodithiol-2-ylidene)amino]-propyl]-2-pyrrolidinone

A solution of 5-chloro-N-methyl-N-phenyl-1,3-benzodithiol-2-iminium iodide (8.39g), N-(3-aminopropyl)-2-pryrrolidinone (2.84g) and anhydrous sodium carbonate (1.06g) in 200 ml of anhydrous dimethylformamide is heated at 120° C under a nitrogen atmosphere for three hours. The reaction mixture is poured into 1000 ml of water and extracted with three 400 ml portions of dichloromethane. The combined organic extracts are washed with two 150 ml portions of water, dried over anhydrous sodium sulfate, and concentrated in vacuo to yield an oil. This oil is chromatographed (900 ml of silica gel) eluting with (1) pentane (2000 ml), (2) pentane/dichloromethane (1:1, 1000 ml), (3) dichloromethane (1000 ml), (4) ethylacetate/dichloromethane (2:8, 1000 ml), and finally (5) methanol/ethyl acetate/dichloromethane (1:2:7, 3000 ml). The oil obtained from elution (5) is dissolved in 120 ml of hexane/dichloromethane (6:1) and cooled to −40° C. The resultant solid is filtered. This solid is then recrystallized from cyclohexane to yield 2.6g of the title compound, melting point 97°-97.5° C.

Anal. Calc'd. for $C_{14}H_{15}ClN_2S_2O$: C, 51.44; H, 4.63; N, 8.57; S, 19.62; Cl, 10.85. Found: C, 51.49; H, 4.33; N, 8.67; S, 19.60; Cl, 10.66.

EXAMPLE 30

1-[(1,3-Benzodithiol-2-ylidene)amino]-2-pyrrolidinone

A mixture of 16.0g of N-(1,3-benzodithol-2-ylidene)-N-methylbenzaminium iodide, 5.8g of N-aminopyrrolidinone·HCl and 4.5g of sodium carbonate is prepared in 120 ml of dimethylformamide. This mixture is heated at 120° C for 3 hours and then poured into water. The water mixrure is extracted with three 300 ml portions of benzene and the benzene extracts are combined and washed with water (500 ml), 5% HCl (500 ml) and brine (300 ml). The benzene extract is then dried over sodium sulfate and concentrated to yield an oil which crystallizes on cooling. The product is recrystallized from cyclohexane to yield 4.4g of the title compound, melting point 122°-124° C.

Anal. Calc'd. for: C, 52.77; H, 4.03; N, 11.19; S, 25.61. Found: C, 52.85; H, 4.28; N, 11.07; S, 25.90.

EXAMPLE 31

N-(1,3-Benzodithiol-2-ylidene)-1H-indol-3-ethanamine

Tryptamine hydrochloride (1.87g), sodium carbonate (1.06g) and N-(1,3-benzodithiol-2-ylidene)-N-methylbenzaminium iodide (3.85g) are combined in 150 ml of anhydrous dimethylformamide and heated at 100° C under a nitrogen atmosphere for one hour. The reaction mixture is poured into 500 ml of water and the solid precipitate is collected by filtration. This solid is dissolved in hot benzene/cyclohexane, treated with charcoal, filtered through Celite, and allowed to crystallize at room temperature. A second recrystallization from cyclohexanebenzene yields 2.4g of the title compound, melting point 149°-149.5° C.

Anal. Calc'd. for $C_{17}H_{14}N_2S_2$: C, 65.77; H, 4.55; N, 9.03; S, 20.66. Found: C, 65.96; H, 4.71; N, 9.30; S, 20.45.

EXAMPLE 32

N-(1,3-Benzodithiol-2-ylidene)-5-methoxy-1H-indole-3-ethanamine

A solution of N-(1,3-benzodithiol-2-ylidene)-N-methylbenzaminium iodide (3.39g), 5-methoxytryptamine hydrochloride (2.0g), and anhydrous sodium carbonate (933 mg) in 100 ml of anhydrous dimethylformamide is heated at 120° C under a nitrogen atmosphere for 2 hours. The reaction mixture is poured into 1500 ml of ice-water. After stirring for 2 hours the slurry is filtered. The solid thus obtained is dissolved in dichloromethane, dried over anhydrous sodium sulfate, and concentrated. The resultant solid is recrystallized twice from pentane/benzene (50:50) to yield 1.5g of the title compound, melting point 139°-139.5° C.

Anal. Calc'd. for $C_{18}H_{16}N_2S_2O$: C, 63.50; H, 4.74; N, 8.23; S, 18.84. Found: C, 63.32; H, 4.82; N, 8.00; S, 19.05.

EXAMPLE 33

N-(1,3-Benzodithiol-2-ylidene)-6-fluoro-1H-indole-3-ethanamine

A solution of N-(1,3-benzodithiol-2-ylidene-N-methylbenzaminium iodide (4.32g), 6-fluorotryptamine (2.0g) and anhydrous sodium carbonate (595 mg) in 100 ml of anhydrous dimethylformamide is heated at 120° C under a nitrogen atmosphere for two hours. The reaction mixture is poured into 500 ml of water and extracted with three 200 ml portions of benzene. The combined benzene extracts are dried over anhydrous sodium sulfate and concentrated. The resultant solid is recrystallized twice from dichloromethane/hexane to yield 1.45g of the title compound, melting point 193° C.

Anal. Calc'd. for $C_{17}H_{13}FN_2S_2$: C, 62.17; H, 3.99; N, 8.53; F, 5.78; S, 19.53. Found: C, 62.44; H, 4.07; N, 8.62; F, 5.69; S, 19.38.

EXAMPLE 34

N-(1,3-Benzodithiol-2-ylidene)-1-[(4-chlorophenyl)methyl]-1H-indole-3-ethanamine Sodium hydride (50% dispersion in mineral oil; 155 mg) is slurried in 5 ml of anhydrous 1,2-dimethoxyethane and treated dropwise with N-(1,3-benzodithiol-2-ylidene)-1H-indol-3-ethanamine (1g, prepared as described in Example 30) in 5 ml of anhydrous 1,2-dimethoxyethane. The mixture is heated at reflux for 3 hours. A solution of α,p-dichlorotoluene (520 mg) in 5 ml of anhydrous 1,2-dimethoxyethane is added dropwise to the refluxing reaction mixture. Refluxing is continued for four hours after addition is complete. The reaction mixture is then poured into water (50 ml) and extracted with two 50 ml portions of dichloromethane. The combined dichloromethane extracts are washed with water and brine, dried over anhydrous sodium sulfate, and concentrated in vacuo. The resultant solid is chromatographed on silica gel (200 ml) eluting with dichloromethanepentane (1:1). The fractions containing product with $R_f=0.8$ (silica gel, dichloromethane) are concentrated. The solid thus obtained is recrystallized from hexane to yield 600 mg of the title compound, melting point 120°–121° C.

Anal. Calc'd. for $C_{24}H_{19}ClN_2S_2$: C, 66.27; H, 4.40; N, 6.44; S, 14.74; Cl, 8.15.

Found: C, 666.50; H, 4.56; N, 6.43; S, 14.50; Cl, 8.19.

EXAMPLE 35

N-(1,3-Benzodithiol-2-ylidene)-1-[(4-chlorophenyl)carbonyl]-1H-indole-3-ethanamine Sodium hydride (57% dispersion in mineral oil; 408 mg) is slurried in 10 ml of anhydrous 1,2-dimethoxyethane and treated dropwise with N-(1,3-benzodithiol-2-ylidene)-1H-indol-3-ethanamine (3g, prepared as described in Example 30) in 15 ml of anhydrous 1,2-dimethoxyethane. The reaction mixture is heated at reflux for 2 hours. A solution of p-chlorobenzoyl chloride (1.69g) in 10 ml of anhydrous 1,2-dimethoxyethane is added dropwise to the refluxing mixture. Refluxing is continued for an additional 4 hours. The reaction mixture is then poured into water (100 ml) and extracted with three 50 ml portions of dichloromethane. The combined dichloromethane extracts are washed with water and brine, dried over anhydrous sodium sulfate and concentrated in vacuo. The residue is chromatographed on silica gel (500 ml) eluting with dichloromethane/pentane (3:2). The fractions containing product with $R_f=0.5$ (silica gel; dichloromethane) are concentrated in vacuo. The solid thus obtained is recrystallized from hexane/dichloromethane to yield 2.1g of the title compound, melting point 135° C.

Anal. Calc'd. for $C_{24}H_{17}ClN_2OS_2$: C, 64.20; H, 3.82; N, 6.24; Cl, 7.91; S, 14.28. Found: C, 64.24; H, 3.71; N, 6.19; Cl, 8.06; S, 14.15.

EXAMPLE 36

N-(5-Chloro-1,3-benzodithiol-2-ylidene)-1H-indole-3-ethanamine

A solution of 5-chloro-N-methyl-N-phenyl-1,3-benzodithiol-2-iminium iodide (8.39g), tryptamine hydrochloride (3.94g) and anhydrous sodium carbonate (2.12g) in 300 ml of anhydrous dimethylformamide is heated at 130° C under a nitrogen atmosphere for 3 hours. After this time the reaction mixture is poured into 1 liter of water and extracted with three 300 ml portions of benzene. The combined benzene extracts are dried over anhydrous sodium sulfate and then concentrated in vacuo to yield an oil. This oil is chromatographed on 600 ml of silica gel eluting first with dichloromethane/pentane (1:1) and finally dichloromethane. The resultant product with $R_f=0.36$ (silica gel-dichloromethane) is recrystallized from dichloromethane/pentane to yield 840 mg of the title compound, melting point 145°–147° C.

Anal. Calc'd. for $C_{17}H_{13}ClN_2S_2$: C, 59.20; H, 3.80; N, 8.12; S, 18.59; Cl, 10.28. Found: C, 59.48; H, 3.79; N, 8.07; S, 18.50; Cl, 10.18.

EXAMPLE 37

3-[(1,3-Benzodithiol-2-ylidene)amino]-2-thioxo-4-thiazolidinone

A solution of N-(1,3-benzodithiol-2-ylidene)-N-methylbenzaminium iodide (3.85g), N-aminorhodanine (1.48g) and anhydrous sodium carbonate (530 mg) in 100 ml of anhydrous dimethylformamide is heated at 120° C under a nitrogen atmosphere for 2 hours. The reaction mixture is then poured into 500 ml of ice/water and left stirring at 4° C for 2 hours. The resultant precipitate is collected by filtration and washed several times with cold water. The solid is air dried to yield 2.0g of crude product. This product is recrystallized from dimethylformamide to yield 1.9g of the title compound, melting point 295°–300° C.

Anal. Calc'd. for $C_{10}H_6N_2OS_4$: C, 40.25; H, 2.03; N, 9.39; S, 42.98.

Found: C, 40.27; H, 2.20; N, 9.30; S, 43.05.

EXAMPLE 38

3-[(1,3-Benzodithiol-2-ylidene)amino]-5-butylidene-3,5-dihydro-2-thioxo-4(5H)-thiazolone A mixture of 1.5g of 3-[(1,3-benzodithiol-2-ylidene)amino]-2-thioxo-4-thiazolidinone (see example 37), butyraldehyde (100 ml), pyridine (1 ml) and acetic acid (2 ml) is heated at reflux for 1 hour. The mixture is then diluted with hexane and the precipitate separated by filtration. The residue is recrystallized from dioxane to yield 1.2 g of material. As this proved to be a mixture of product and starting material, the compound was mixed again with butyraldehyde (100 ml) and pyridinium acetate (3 ml) and heated at reflux for 24 hours. Worked up as before and crystallized from amyl alcohol the yield of the title compound is 900 mg, melting point 236°–238° C.

Anal. Calc'd. for $C_{14}H_{12}N_2OS_4$: C, 47.70; H, 3.43; N, 7.95; S, 36.38. Found: C, 47.58; H, 3.40; N, 7.69; S, 36.28.

EXAMPLE 39

3-[(5-Chloro-1,3-benzodithiol-2-ylidene)amino]-2-thioxo-4-thiazolidinone

A mixture of the methiodide of 5-chloro-N-methyl-N-phenyl-1,3-benzodithiol-2-iminium iodide (1.9 g), sodium carbonate (121 mg), N-aminorhodanine (338 mg) and dimethylformamide (20 ml) is heated at 50° C for 3 hours. The mixture is poured into water and the precipitate which forms is filtered and washed with water. The product is recrystallized from dimethylformamide to yield 600 mg of the title compound, melting point 312°–314° C.

Anal. Calc'd. for $C_{10}H_5ClN_2OS_4$: C, 36.08; H, 1.51; N, 8.42; S, 38.53; Cl, 10.65. Found: C, 36.26; H, 1.45; N, 8.68; S, 38.71; Cl, 10.73.

EXAMPLE 40

3-[(1,3-Benzodithiol-2-ylidene)amino]-5-(phenylmethylene)-2-thioxo-4-thiazolidinone A mixture of 2.0g of 3-[(1,3-benzodithiol-2-ylidene)amino]-2-thioxo-4-thiazolidinone (see example 37), benzaldehyde (20 ml, excess) and pyridinium acetate (5 ml) is prepared and heated at 120° C for 3 days under nitrogen with stirring. The mixture is then cooled, diluted with ether and filtered. The residue is washed with water and recrystallized from dimethylformamide to yield 2.2 g of the title compound, melting point 288°–289° C.

Anal. Calc'd. for $C_{17}H_{10}N_2OS_4$: C, 52.82; H, 2.61; N, 7.25; S, 33.18. Found: C, 53.02; H, 2.74; N, 7.07; S, 33.04.

EXAMPLE 41

3-[(1,3-Benzodithiol-2-ylidene)amino]-5-pentylidene-2-thioxo-4-thiazolidinone

A slurry of 2.0g of 3-[(1,3-benzodithiol-2-ylidene)amino]-2-thioxo-4-thiazolidinone (see example 37), valeraldehyde (10 ml, excess) and acetic acid/piperidine (2:1) (10 drops) in anhydrous slyme (400 ml) is heated at reflux for eighteen hours. The reaction mixture is chilled in an ice bath and the resultant precipitate collected by filtration. This precipitate (1.6 g) is recrystallized from 50 ml of dimethylformamide to yield 1.1 g of the title compound, melting point 210°–212° C.

Anal. Calc'd. for $C_{15}H_{14}N_2OS_4$: C, 49.15; H, 3.85; N, 7.64; S, 34.99. Found: C, 49.32; H, 3.74; N, 7.39; S, 34.73.

EXAMPLE 42

3-[(1,3-Benzodithiol-2ylidene)amino]-5-tetradecyclidene-2-thioxo-4-thiazolidinone A slurry of 2.0g of 3-[(1,3-benzodithiol-2-ylidene)amino]-2-thioxo-4-thiazolidinone (see example 37), tetradecyl aldehyde (20 g, excess) and acetic acid/piperidine (10 drops) in anhydrous glyme (400 ml) is heated at reflux for eighteen hours. The reaction mixture is cooled in an ice bath and the resultant precipitate collected by filtration. This precipitate is recrystallized from 75 ml of dimethylformamide to yield 2 g of the title compound, melting point 180°–181° C.

Anal. Calc'd. for $D_{24}H_{32}N_2OS_4$: C, 58.50; H, 6.55; N, 5.68; S, 26.02. Found: C, 58.62; H, 6.42; N, 5.48; S, 26.28.

EXAMPLE 43

5-[3-[(1,3-Benzodithiol-2-ylidene)amino]-4-oxo-2-thioxo-5thiazolylidene]pentanoic acid, methyl ester A slurry of 2.98g of 3-[(1,3-benzodithiol-2-ylidene)amino]-2-thioxo-4-thiazolidinone (see example 37), methyl-5-pentanaloate (10 g, excess) and acetic acid/piperidine (10 drops) in 400 ml of anhydrous glyme is heated at reflux for eighteen hours. The reaction mixture is chilled in an ice bath and the resultant precipitate collected by filtration. The yellow product is recrystallized from dimethylformamide to yield 2.3g of the title compound, melting point 210° C.

Anal. Calc'd. for $C_{16}H_{14}N_2O_3S_4$: C, 46.81; H, 3.44; N, 6.82; S, 31.24. Found: C, 46.91; H, 3.29; N, 6.99; S, 31.28.

EXAMPLE 44

3-[(1,3-Benzodithiol-2-ylidene)amino]-5-octylidene-2-thioxo-4-thiazolidinone

A slurry of 2.0g of 3-[(1,3-benzodithiol-2-ylidene)amino]-2-thioxo-4-thiazolidinone (see example 37), octanal (15 ml, excess) and acetic acid/piperidine (10 drops) in anhydrous glyme (400 ml) is heated at reflux for 18 hours. The reaction mixture is chilled in an ice bath and the resultant precipitate collected by filtration. The precipitate is recrystallized twice from dimethylformamide to yield 1.02g of the title compound, melting point 185° C.

Anal. Calc'd. for $C_{18}H_{20}N_2OS_4$: C, 52.91; H, 4.93; N, 6.86; S, 31.38 Found: C, 52.97; H, 4.78; N, 6.92; S, 31.27

EXAMPLE 45

3-(1,3-Benzodithiol-2-ylideneamino)-5-(2-phenylethylidene)-2-thioxo-4-thiazolidinone A slurry of 2.98g of 3-[(1,3-benzodithiol-2-ylidene)amino]-2-thioxo-4-thiazolidinone (see example 37), phenylacetaldehyde (10 ml, excess) and acetic acid/piperidine (10 drops) in 600 ml of anhydrous glyme is heated at reflux for 4 days. The reaction mixture is filtered while hot, and the solid is collected and recrystallized from dimethylformamide to yield 1.78 g of the title compound, melting point 233°–234° C.

Anal. Calc'd. for $C_{18}H_{12}N_2OS_4$: C, 53.98; H, 3.02; N, 6.99; S, 32.02. Found: C, 54.05; H, 2.90; N, 7.23; S, 31.84.

EXAMPLE 46

3-[(1,3-Benzodithiol-2-ylidene)amino]-2-thioxo-5-[[3-(trifluoromethyl)phenyl]methylene]-4-thiazolidinone A slurry of 3-[(1,3-benzodithiol-2-ylidene)amino]-2-thioxo-4-thiazolidinone (see example 37), m-trifluoromethylbenzaldehyde (10 ml, excess) and acetic acid/piperidine (1 ml) in 250 ml of anhydrous glyme is heated at reflux for seven days. The reaction mixture is concentrated in vacuo and the oily residue extracted with hexane. The solid thus obtained is slurried in 1000 ml of dichloromethane and stirred at room temperature overnight. The slurry is filtered and the filtrate concentrated in vacuo. The solid residue thus obtained is recrystallized from dimethylformamide to yield 500 mg of the title compound, melting point 268°–269° C.

Anal. Calc'd. for $C_{18}H_9N_2S_4F_3O$: C, 47.57; H, 2.00; N, 6.16; S, 28.21; F, 12.54. Found: C, 47.83; H, 1.91; N, 6.36; S, 28.43; F, 12.78.

thyl)morpholine and the compound listed in column II for N-(1,3-benzodithiol-2-ylidene)-N-methylbenzaminium iodide, yields the compound listed in column III.

| Column I | Column II | Column III |
|---|---|---|
| N-(aminopropyl)thiamorpholine | 5-methyl-N-methyl-N-N-phenyl-1,3-benzodithiol-2-iminium iodide | N-(5-methyl-1,3-benzodithiol-2-ylidene)-4-thiamorpholine-propaneamine |
| N-(aminoethyl)piperazine | 5-hydroxy-N-methyl-N-phenyl-1,3-benzodithiol-2-iminium iodide | N-(5-hydroxy-1,3-benzodithiol-2-ylidene)-1-piperazine-ethaneamine |
| N-(aminoethyl)pyrrolidine | 5-bromo-N-methyl-N-phenyl-1,3-benzodithiol-2-iminium iodide | N-(5-bromo-1,3-benzodithiol-2-ylidene)-1-pyrrolidine-ethaneamine |

EXAMPLE 47

3-[(5-Methoxy-1,3-benzodithiol-2-ylidene)amino]-2-thioxo-4-thiazolidinone

A slurry of 4.15g of N-(5-methoxy-1,3-benzodithiol-2-ylidene)-N-methylbenzaminium iodide, N-aminorhodanine (1.48 g, 0.01 mole) and sodium carbonate (530 mg, 0.005 mole) in 100 ml of dimethylformamide is heated at 120° C for 2 hours. The reaction mixture is chilled in an ice bath and the resultant precipitate collected by filtration. The product is recrystallized from dimethylformamide to yield 2.23 g of the title compound, melting point 254°-255° C.

Anal. Calc'd. for $C_{11}H_8N_2O_2S_4$: C, 40.23; H, 2.46; N, 8.53; S, 39.05. Found: C, 40.27; H, 2.37; N, 8.70; S, 38.83.

EXAMPLE 48

2-Thioxo-3-[[5-(trifluoromethyl)-1,3-benzodithiol-2-ylidene]amino]-4-thiazolidinone A slurry of 3.0g of N-methyl-N-[5-(trifluoromethyl)-1,3-benzodithiol-2-ylidene]benzaminium iodide, N-aminorhodanine (982 mg) and sodium carbonate (351 mg) in 100 ml of anhydrous dimethylformamide is heated at 120° C for 2 hours. The reaction mixture is chilled in an ice bath and the resultant precipitate collected by filtration. This product is recrystallized from dimethylformamide to yield 570 mg of the title compound, melting point 285°-288° C.

Anal. Calc'd. for $C_{11}H_5F_3N_2OS_4$: C, 36.06; H, 1.38; N, 7.65; S, 35.00; F, 15.56. Found: C, 36.14; H, 1.26; N, 7.89; S, 35.16; F, 15.61.

EXAMPLE 49

3-[(5-Nitro-1,3-benzodithiol-2-ylidene)amino]-2-thioxo-4-thiazolidinone

A slurry of 4.24g of N-methyl-N-(5-nitro-1,3-benzodithiol-2-ylidene)benzaminium iodide, N-aminorhodanine (1.47 g), and sodium carbonate (523 mg) in 100 ml of dimethylformamide is heated at 120°-140° C for two hours. The reaction solution is chilled in an ice water bath and the resultant precipitate collected by filtration. The precipitate is recrystallized twice from dimethylformamide to yield 1.2 g of the title compound, melting point 315° C.

Anal. Calc'd. for $C_{10}H_5N_3O_3S_4$: C, 34.98; H, 1.47; N, 12.24; S, 37.34. Found: C, 35.20; H, 1.36; N, 12.49; S, 37.62.

EXAMPLES 50-52

Following the procedure of example 25, but substituting the compound listed in column I for N-(aminoe-

What is claimed is:

1. A compound having the formula

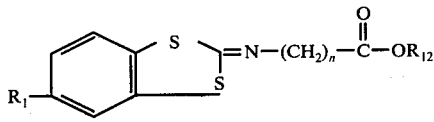

or a pharmaceutically acceptable salt thereof, wherein $R_1$ is hydrogen, halogen, trifluoromethyl, alkyl, alkoxy, nitro, amino or hydroxy; $R_{12}$ is hydrogen or alkyl; and n is 0, 1, 2, 3, 4 or 5; wherein the terms "alkyl" and "alkoxy" refer to groups having 1 to 4 carbon atoms.

2. A compound in accordance with claim 1 wherein $R_1$ is hydrogen.

3. A compound in accordance with claim 1 wherein $R_1$ is halogen.

4. A compound in accordance with claim 1 wherein n is 0.

5. A compound in accordance with claim 1 wherein n is 1, 2, 3, 4 or 5.

6. A compound in accordance with claim 1 wherein $R_{12}$ is hydrogen.

7. A compound in accordance with claim 1 wherein $R_{12}$ is alkyl.

8. The compound in accordance with claim 1 having the name [(1,3-benzodithiol-2-ylidene)amino]acetic acid, ethyl ester.

9. The compound in accordance with claim 1 having the name 3-[(1,3-benzodithiol-2-ylidene)amino]-propanoic acid, ethyl ester.

10. The compound in accordance with claim 1 having the name [(1,3-benzodithiol)-2-ylidene)amino]acetic acid.

11. The compound in accordance with claim 1 having the name 3-[(1,3-benzodithiol-2-ylidene)amino]-propanoic acid.

12. The compound in accordance with claim 1 having the name 4-[(1,3-benzodithiol-2-ylidene)amino]butanoic acid, ethyl ester.

13. The compound in accordance with claim 1 having the name [(1,3-benzodithiol-2-ylidene)amino]butanoic acid.

14. The compound in accordance with claim 1 having the name 3-[(1,3-benzodithiol-2-ylidene)amino]-propanoic acid, methyl ester.

15. The compound in accordance with claim 1 having the name 3-[(1,3-benzodithiol-2-ylidene)amino]-propanoic acid, 1-methylethyl ester.

16. The compound in accordance with claim 1 having the name 3-[(1,3-benzodithiol-2-ylidene)amino]propanoic acid, butyl ester.

17. The compound in accordance with claim 1 having the name 3-[(5-chloro-1,3-benzodithiol-2-ylidene)amino]butanoic acid, ethyl ester.

18. The compound in accordance with claim 1 having the name 3-[(1,3-benzodithiol-2-ylidene)amino]butanoic acid, methyl ester.

19. The compound in accordance with claim 1 having the name 3-[(1,3-benzodithiol-2-ylidene)amino]butanoic acid, 1-methylethyl ester.

20. The compound in accordance with claim 1 having the name 3-[(1,3-benzodithiol-2-ylidene)amino]butanoic acid, butyl ester.

21. The compound in accordance with claim 1 having the name 3-[(5-chloro-1,3-benzodithiol-2-ylidene)amino]propanoic acid, ethyl ester.

* * * * *

UNITED STATES PATENT AND TRADEMARK OFFICE
CERTIFICATE OF CORRECTION

PATENT NO. : 4,107,175                           Page 1 of 3
DATED      : August 15, 1978
INVENTOR(S) : Peter W. Sprague, et al It is certified that error appears in the above-identified patent and that said Letters Patent are hereby corrected as shown below:

Column 1, line 7, "Benzodirthiolanes" should read --Benzodithiolanes--

Column 1, next to first structure insert --I--

Column 2, line 53, "od" should read --of--

Column 4, line 4, "abovedescribed" should read --above-described--

Column 4, line 68, "methyl-benzaminium" should read --methylbenzaminium--

Column 5, line 31, "tims" should read --times--

Column 6, line 36, "benzminium" should read --benzaminium--

Column 6, delete lines 40 to 52

Column 7, line 47, "chromatogrphed" should read --chromatographed--

Column 8, line 14, "2ylidene" should read --2-ylidene--

Column 8, line 37, "2ylidene" should read --2-ylidene--

Column 9, line 2, "gell" should read --gel--

Column 10, line 1, "1.1" should read --1:1--

Column 10, line 2, "the" should read --The--

Column 10, line 52, "dichlormethane" should read

UNITED STATES PATENT AND TRADEMARK OFFICE
CERTIFICATE OF CORRECTION

PATENT NO. : 4,107,175           Page 2 of 3
DATED      : August 15, 1978
INVENTOR(S): Peter W. Sprague, et al It is certified that error appears in the above-identified patent and that said Letters Patent are hereby corrected as shown below:

--dichloromethane--

Column 11, line 8, "pentant" should read --pentane--

Column 11, line 22, "[(," should read --[(1--

Column 11, line 24, insert --ylidene)-- after 2-

Column 11, line 50, "methylbanzaminium" should read --methylbenzaminium--

Column 12, line 6, "zo-dithiol" should read --zodithiol--

Column 12, line 66, "etheral" should read --ethereal--

Column 13, line 49, "wwashed" should read --washed--

Column 14, line 55, "bisethanol" should read --bis-ethanol--

Column 15, line 64, "solidifices" should read --solidifies--

Column 16, line 39, "combine" should read --combined--

Column 17, line 40, "8530" should read --(530--

Column 18, line 39 after "nitrogen" should read -- atmosphere --.
Column 18, line 4, after "poured" should read -- into --.
Column 19, line 47, "666.50" should read --66.50--

UNITED STATES PATENT AND TRADEMARK OFFICE
CERTIFICATE OF CORRECTION

PATENT NO. : 4,107,175  Page 3 of 3
DATED : August 15, 1978
INVENTOR(S) : Peter W. Sprague, et al It is certified that error appears in the above-identified patent and that said Letters Patent are hereby corrected as shown below:

Column 21, line 45, "slyme" should read --glyme--

Column 22, line 1, "D" should read --C--

Column 22, line 6, insert a hyphen after "5"

Columns 23 and 24, in the table, insert --50--, --51--, --52-- in front of the respective examples Signed and Sealed this Seventeenth Day of April 1979

[SEAL]

Attest:

RUTH C. MASON
Attesting Officer

DONALD W. BANNER
Commissioner of Patents and Trademarks